United States Patent
Kleinert

(10) Patent No.: US 7,694,566 B2
(45) Date of Patent: Apr. 13, 2010

(54) METHOD OF EVALUATING ULTRASONIC SIGNALS OF A FLAW IN A WORKPIECE

(75) Inventor: Wolf Kleinert, Bonn (DE)

(73) Assignee: GE Inspection Technologies, GmbH, Hurth (DE)

(*) Notice: Subject to any disclaimer, the term of this patent is extended or adjusted under 35 U.S.C. 154(b) by 657 days.

(21) Appl. No.: 10/539,270

(22) PCT Filed: Nov. 4, 2003

(86) PCT No.: PCT/DE03/03654

§ 371 (c)(1),
(2), (4) Date: Apr. 9, 2007

(87) PCT Pub. No.: WO2004/057326

PCT Pub. Date: Jul. 8, 2004

(65) Prior Publication Data

US 2007/0240513 A1 Oct. 18, 2007

(30) Foreign Application Priority Data

Dec. 18, 2002 (DE) .................. 102 59 658

(51) Int. Cl.
*G01N 29/06* (2006.01)

(52) U.S. Cl. ............... 73/606; 73/598; 73/602; 73/615; 73/627

(58) Field of Classification Search ........... 73/606, 73/598, 600, 602, 63, 615, 618, 625, 626–628
See application file for complete search history.

(56) References Cited

U.S. PATENT DOCUMENTS 3,996,792 A * 12/1976 Kubota et al. ........... 73/611
4,137,779 A * 2/1979 Wustenberg et al. ........ 73/627
4,375,165 A * 3/1983 de Sterke ................ 73/622

(Continued)

FOREIGN PATENT DOCUMENTS

DE 198 03 615 A1 8/1999

(Continued)

OTHER PUBLICATIONS

Grohs, B. et al., Characterization of Flaw Location, Shape, and Dimensions with the ALOK System, Materials Evaluation, vol. 40, Jan. 1982.

(Continued)

*Primary Examiner*—J M Saint Surin
(74) *Attorney, Agent, or Firm*—Novak Druce+Quigg; J. Rodman Steele, Jr.

(57) ABSTRACT

The invention relates to a method for representing echo signals that are obtained with the aid of an ultrasonic test apparatus used for non-destructively testing a test piece. Said ultrasonic test apparatus comprises a probe, especially an angled probe, a monitor with a display device for representing the received echo signals in an cross-sectional image such that at least one front face and a back wall of the test piece can be recognized. A flaw is detected from different arrangements of the angular probe, represented, and an error signal is determined. The test images are stored and then represented in a superimposed manner in an evaluation image such that the first and the second error signal can be recognized.

9 Claims, 2 Drawing Sheets

U.S. PATENT DOCUMENTS

Figure 1:
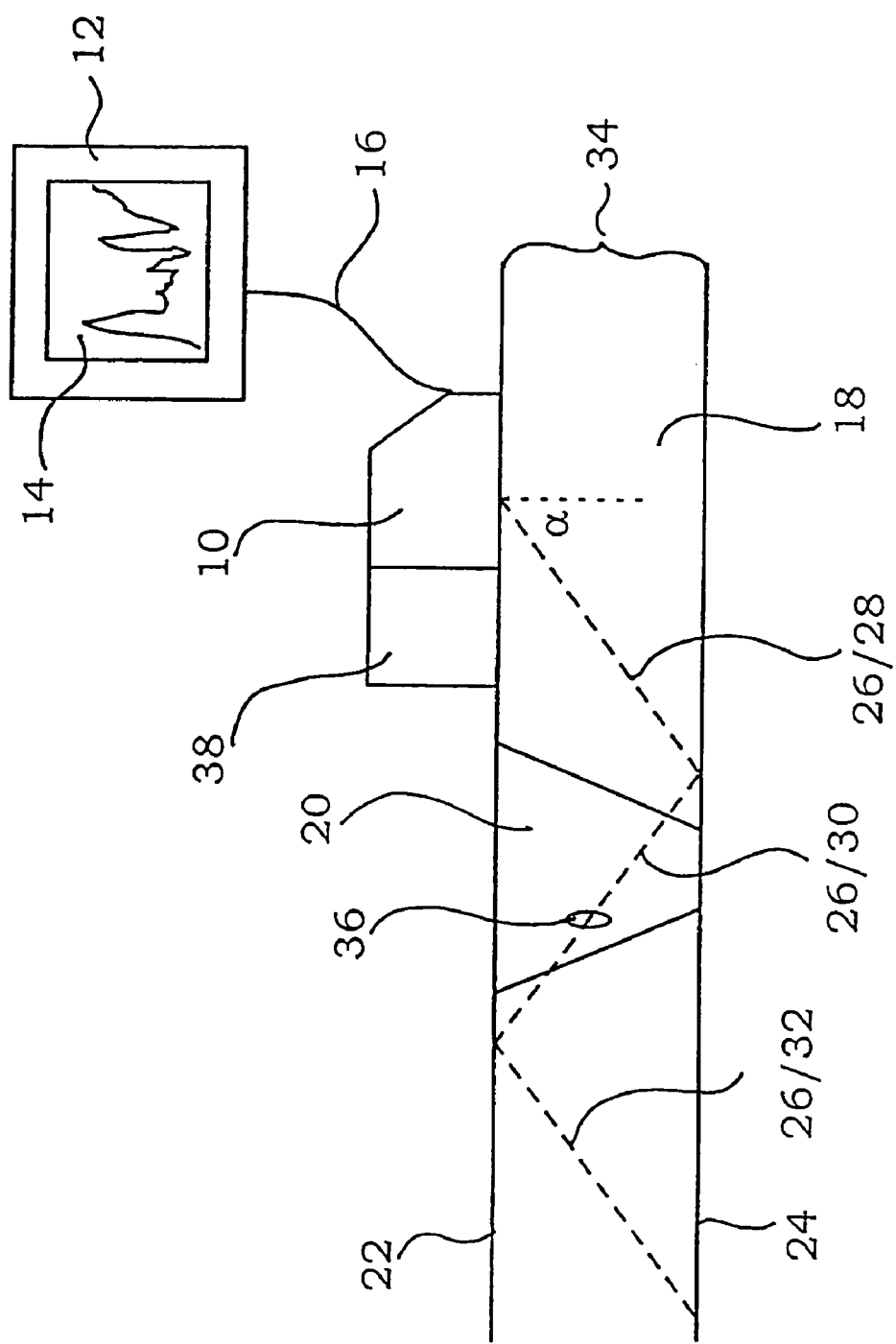

| | | | | |
|---|---|---|---|---|
| 4,467,654 | A * | 8/1984 | Murakami et al. | 73/640 |
| 4,475,394 | A * | 10/1984 | Takeda et al. | 73/598 |
| 4,663,727 | A * | 5/1987 | Saporito et al. | 702/39 |
| 4,817,016 | A * | 3/1989 | Thompson et al. | 702/39 |
| 4,866,614 | A * | 9/1989 | Tam | 600/437 |
| 4,884,246 | A * | 11/1989 | Heyser et al. | 367/7 |
| 5,056,368 | A * | 10/1991 | Kawasaki et al. | 73/642 |
| 5,349,860 | A * | 9/1994 | Nakano et al. | 73/597 |
| 5,392,652 | A * | 2/1995 | Levesque et al. | 73/629 |
| 5,398,551 | A * | 3/1995 | Kawasaki et al. | 73/593 |
| 5,497,662 | A * | 3/1996 | Dykes | 73/634 |
| 5,538,004 | A * | 7/1996 | Bamber | 600/443 |
| 6,234,025 | B1 | 5/2001 | Gieske et al. | |
| 6,673,020 | B2 * | 1/2004 | Okada et al. | 600/454 |
| 6,931,931 | B2 * | 8/2005 | Graff et al. | 73/622 |
| 7,472,598 | B2 * | 1/2009 | Kleinert | 73/627 |
| 2006/0016263 | A1 * | 1/2006 | Kleinert | 73/620 |

FOREIGN PATENT DOCUMENTS

| | | |
|---|---|---|
| DE | 100 58 174 A1 | 5/2002 |
| GB | 1 239 970 A | 7/1971 |

OTHER PUBLICATIONS

Deutsch, V., Rechnergestutzte Fehlerbeschreibung, Ultraschallprufung, 1997, pp. 133-141.

Schlengermann, U., Characterization of Reflectors by Ultrasonic Methods, NDTNET, vol. 1, No. 12, Dec. 1996, pp. 1-8.

Schlengermann, U., Beitrag zur ErsatzfehlergroBenbestimmung beim Ultraschallprufen nach der Tandemmethode, Schweiben und Schneiden, vol. 26, No. 5, 1974, pp. 169-172.

* cited by examiner

METHOD OF EVALUATING ULTRASONIC SIGNALS OF A FLAW IN A WORKPIECE

The invention relates to a method of displaying echo signals obtained for non-destructive inspection of a test body using an ultrasonic inspection apparatus.

Suitable inspection apparatus have been known for ultrasonic non-destructive inspection of a workpiece. Generally, the reader is referred to the German book by J. and H. Krautkrämer, Ultrasonic Testing of Materials, sixth edition.

The angle beam probe delivers high-frequency sound pulses (about 1-10 MHz) that are sent into the workpiece to be tested and are reflected from the front surface back to the angle beam probe on the one side and on the other side penetrate the workpiece where they are reflected at least once from a rear wall of the workpiece. The sound waves are reflected off inner inhomogeneities such as material flaws and are again received by the angle beam probe and processed in the ultrasonic apparatus.

The pulse-echo method is used. The angle beam probe delivers ultrasonic pulses preferably periodically and receives later the echo signals of these delivered ultrasonic pulses. Generally, the echo signal from the front surface is a particularly strong signal that is stronger than the other echo signals. The other echo signals originate from the workpiece and more specifically from the rear wall of the workpiece. Inasmuch, the inspection method is suited for workpieces the front surface of which extends substantially parallel to the rear wall so that the ultrasonic pulse is reflected several times back and forth within the workpiece.

The angle beam probe is disposed next to the to-be-tested area and the sound signal is insonified into the area of concern from the side so to say. This is the case with ultrasonic inspection of weld seams for example.

An angle beam probe operates over a plexiglass shoe with oblique insonification. The ultrasound wave enters the material until it is partially or completely reflected from an interface. If the reflecting surface is normal to the direction of propagation, the sound wave will be reflected in its initial direction and will reach, after a certain travel time, a piezoelectric crystal disposed in the angle beam probe that converts it back into an electrical pulse. The return ultrasound is again reflected from the interface crystal-workpiece surface with this small sound portion travelling a second time through the workpiece. Thus, what is termed an echo sequence is produced by multiple reflection from interfaces (rear wall of the part being tested or flaw) when using the pulse-echo method.

Accordingly, when the test body has no flaws, the sound is reflected between the front surface and the rear wall of the test body and continues to penetrate the test body at a certain angle in the direction away from the angle beam probe.

When inspecting weld seams, the angle beam probe is caused to move along the weld seam until a maximal flaw echo signal is produced. The echo signals received are directly displayed on the monitor. Generally, they are displayed as what is termed an A-scan in which the voltage values of the echo signals received are plotted down the side of the scan whereas time is plotted on the longitudinal axis. As the sound wave is reflected several times back and forth between the front surface and the rear wall, a sequence of uniformly spaced echo signals are produced the amplitude of which generally decreases with increasing time. The discrete back and forth movements, meaning the distance the sound travels from the front surface to the rear wall and back is referred to as a leg. Starting from the angle beam probe, a first leg, which extends at an incline from the front surface toward the rear wall, is first produced. From there, the sound is reflected, forming a second leg that extends from the rear wall toward the front surface, and so on.

The position determination of a reflector (flaw) within the test part is calculated from the known and measured data. The echo amplitude is used for estimation of the flaw size. This is not reliably possible though since the echo amplitude is subject to many more influences than the travel time of the sound.

Methods are known that allow for estimation of the flaw size or the discontinuity. Using these methods, the size (diameter) of a model reflector (circular disc, cylindrical reflector) is estimated. The thus determined size is not identical with the actual flaw size and is therefore referred to as the equivalent diameter of the circular disc or of the transverse hole. Using circular disc reflectors, the term "equivalent reflector size" has gained common acceptance. The actual flaw size does not coincide with the equivalent reflector size because the sound portions reflected from a natural flaw are additionally influenced by the shape, the orientation and the nature of the flaw's surface. Since more extensive tests are complicated and difficult to put into practice using manual ultrasonic inspection, most of the specifications and guidelines for ultrasonic testing link the criteria for recording defects with a certain equivalent reflector size. This signifies that the inspector determines whether a defect found is equal to, or larger than, the equivalent reflector size indicated as the limit value (recording limit) in the control system. He must moreover perform further tests related for example to recording length, echo dynamics, and so on; these tests will not be discussed herein, though.

The problem that arises, particularly when using an angle beam probe for inspection, is that if, in an extreme case, the defect such as an air bubble is oriented parallel to the sound path, the sound will very likely miss the defect. If, by contrast, the sound hits the defect, it will be reflected and the signal recorded. On the basis of the equivalent reflector size, the defect obtained appears very small on the monitor. It does not really show that the defect extends much farther in the direction of the sound path.

This is where the invention comes in. Its object is to improve evaluation of ultrasonic signals obtained for non-destructive inspection of a test body using an ultrasonic inspection apparatus. It aims at facilitating assertions about the orientation and nature of the flaw such as about whether the flaw is planar or voluminous. The inspector is to be given the possibility to recognize quickly, readily and reliably whether the signal found is indicative of a flaw of some relevance.

In accordance with the invention, this is achieved by a method having the features recited in claim 1.

As used herein, the term flaw is not only meant literally, that is, to refer to discontinuities, but is also to be construed as a significant signal. Accordingly, the invention also includes finding any relevant location in a test body.

The result of the measurement is not or not only displayed as what is termed an A-scan; the geometry of the test body is also shown on the display. The geometry of the test body is particularly obvious when the test body is displayed in cross section. This is possible if the wall thickness of the test body is known. As the insonification angle at which the sound is insonified from the angle beam probe into the test body is known, it is also possible to display the path of the sound travelling through the test body. The display is particularly informative when the dimensions of relevant areas to be tested can be included in the cross-sectional view. In particular when testing weld seams, this is helpful and readily possible. The representation obtained is for example a cross-sectional view of two steel plates that are joined together at their end by a weld seam. Accordingly, the weld seam between the two steel plates is shown by lenses. In this cross-sectional view, a detected flaw is shown directly true to scale using the comparative method.

Accordingly, it can be seen along which path the sound travels through the test body starting from the angle beam probe and in which leg or at which other place the sound hits the flaw. As already explained, the prerequisite for such a system is the known insonification angle and the known wall thickness of the test body. The sound path for one leg and, as a result thereof, the transition from one leg to the next or the point at which the sound is reflected from the front surface or from the rear wall can be readily calculated from this information.

From this representation, the inspector can gather relevant information about the flaw, more specifically about its size and orientation, if he proceeds in accordance with the method described herein after.

At first, upon finding a flaw or a corresponding signal on the monitor, the inspector accordingly grows said flaw or signal and stores the optimized image shown on the display. The flaw is thereby estimated using the comparative method, that is, on the basis of an equivalent reflector size, and is displayed true to scale on the display by a flaw signal. The displayed image only shows the flaw as it appears on the basis of the insonification direction. Depending on its orientation, the flaw can however be much larger than it appears in this first image, more specifically if its main orientation extends substantially parallel to the sound path.

Therefore, in the next method step, ultrasonic inspection is repeated with the angle beam probe being in another position. This second inspection may for example be performed from the opposite side of the flaw. It may also make sense to dispose the angle beam probe so as to be offset about 90° with respect to the flaw. A new image is produced and the flaw again estimated on the basis of an equivalent reflector size and displayed as a flaw signal. This image is also stored.

Next, the stored images are shown simultaneously on the display, that is to say, they are superimposed so to speak. The detected flaw is then displayed in the form of two flaw signals obtained from the two equivalent reflector sizes, this permitting the inspector to recognize at first sight how the flaw extends in various directions. A two-dimensional image of the flaw is thus obtained.

The accuracy of the method of the invention can be increased by inspecting the flaw not only from two, but from a plurality of directions and by displaying a corresponding number of superimposed scans.

It may also be advantageous to maintain the direction of the angle beam probe relative to the flaw while reducing or increasing the distance therebetween. As a result, one achieves that the flaw is located in another leg of the sound path and that the sound hits the flaw at another angle. In order to make it easier for the inspector to orient the angle beam probe, the sound path is advantageously shown on the display in such a manner that it can be readily seen from which leg the echo signals originate. This means that the various legs are for example shown by a kind of line that is characteristic for a respective one of the legs or that the background of the discrete legs is shown in a characteristic manner for example.

In another advantageous implementation variant, the flaw detected on the basis of the comparative method is also represented in different ways in every stored image. Accordingly, it can be readily seen on which leg or which direction the detected flaw signal is based. This facilitates estimation or interpretation of the data, in particular in the illustration in which the detected flaw signals are shown superimposed.

In a particular advantageous implementation variant, the ultrasonic apparatus, or a computer mounted therein, calculates, from the flaw variables already detected from various directions, a top view of the flaw, an representation of the flaw in the plane of the test body so to speak. Advantageously, this top view can be displayed simultaneously with the cross-sectional view on the display so that the display is divided into two views. Preferably, the relevant region such as the weld seam is shown by lines in the top view image also. Advantageously, the length of the flaw in the plane of the test body can be estimated automatically using the half-value technique.

In the top view, the flaw is preferably shown in an x-y diagram on which the width is plotted on the one axis and the length of the flaw is plotted on the other axis in millimetres or in another suitable unit. In accordance with the invention, scaling is determined automatically when computing this top view representation.

As a result, it is in principle possible to generate a three-dimensional representation of the flaw.

Advantageously, when storing the various relevant cross-sectional images, the A-scan is also stored in the background.

Advantageously, the method of the invention can be further improved by using a colour display. As a result, it is possible to represent the respective flaw signals detected from the respective positions of the angle beam probe in a characteristic colour so that the quality of the representation in terms of visibility is improved. The various legs of the sound path may also be represented in colour which also makes it easier to distinguish them. Beside LCD displays, other colour monitors such as plasma displays have also proved efficient.

In another advantageous implementation variant, the angle beam probe comprises a calliper for recording the zero point position at the beginning of the inspection procedure. This means that inspection starts at a defined location on the test body, said location being stored in the system. This permits to later reconstruct relevant positions of the angle beam probe on the basis of the stored data. For this purpose, the angle beam probe comprises means that serve to indicate the respective position on the surface of the body to be tested with respect to the location at the beginning of measurement. This can be performed using for example a digital camera that is solidly connected to the housing of the angle beam probe. It is oriented so as to capture the surface of the body to be tested. It is anticipated that it delivers an image of this surface in proximity to the very location at which a central beam of the active sound element passes through the surface. At intervals, an electronic image of the surface portion which is respectively located beneath the lens of the digital camera, which accordingly lies in the object plane, is captured by means of this digital camera. The portion may have dimensions of a few millimetres for example such as 2×2 or 4×4 mm. Preferably, at given fixed intervals, the digital camera captures an image of the respective surface portion. The reader is referred in this context to the application DE 100 58 174 A1 of the applicant.

If the weld seam geometry is known and stored in the ultrasonic inspection apparatus or in the computer, both spatial limits and limits with respect to the amplitude to be taken into consideration may be entered. If, at the beginning of the measurement, the zero point position has been located, the distance of the angle beam probe from the weld seam can be computed any time based on the leg length or the wall thickness and on the insonification angle. Accordingly, it is possible to represent on the monitor, any time and independent of the position of the angle beam probe, the mere region of the weld seam, using an active aperture.

Using an active aperture as described, it is also possible to select the flaws to be represented in the top view. It may for example make sense to only represent a flaw when it has a certain size. In terms of flaw size, a minimal and maximal amplitude to be taken into consideration are entered as the aperture. It is also possible to only enter the maximal amplitude and it is then further determined that a flaw will only be shown when it exceeds the half-maximal amplitude.

Figure 2:
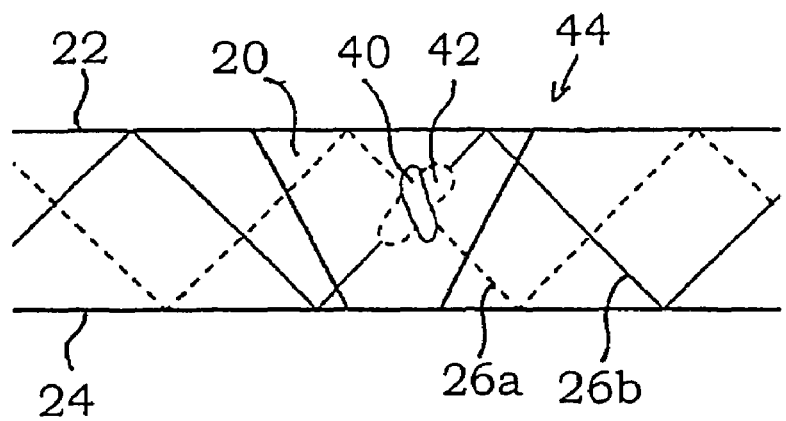
Figure 3:
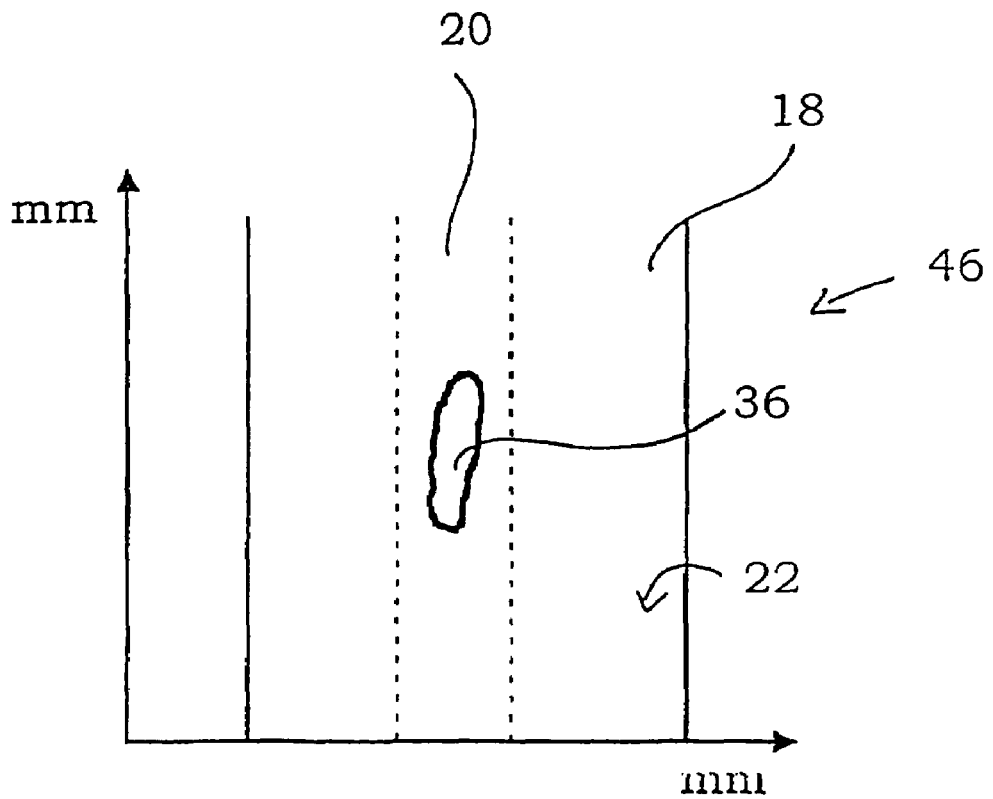

Other features and advantages of the invention will become more apparent upon reviewing the claims and the following non restrictive description of embodiments of the invention, given by way of example only with reference to the drawing. In said drawing:

FIG. 1 is a schematic diagram of the sound path of an ultrasonic signal taking departure from an angle beam probe and passing through a test body, FIG. 2 shows an exemplary representation of two measurement images in an evaluation image captured in accordance with the invention, FIG. 3 is a top view of an exemplary representation of the measurement data obtained.

FIG. 1 is a cross-sectional view of the basic structure of an ultrasound measurement using an angle beam probe 10 as the ultrasonic measurement apparatus. The angle beam probe 10, which includes a transmitter and a receiver, is connected by a wire cable 16 to a monitor 12, which in turn comprises a display 14. It may also be envisaged to use another kind of connection such as a wireless connection instead of the wire cable 16. The angle beam probe 10 may also be configured so that the transmitter and the receiver are arranged separately from each other. In the following description however, it is assumed that the transmitter and the receiver are located within the angle beam probe 10 and that measurement is performed using the echo-pulse method.

The test body 18 here is a portion of a steel plate that is connected through a weld seam 20 to a second steel plate. The test body 18 comprises a front surface 22 and a rear wall 24 with the angle beam probe 10 being disposed on the front surface 22. Between the front surface 22 and the rear wall 24, a sound path 26 is shown by a line. Taking departure from the angle beam probe 20, the sound is first insonified obliquely into the test body 18 at a certain angle α in the form of transmitter pulses, forms a first leg 28, is then reflected from the rear wall 24, forms a second leg 30, returns back to the front surface 22, is reflected again and forms a third leg 32 and so on. In the exemplary representation, the sound path 26 intersects the weld seam 20 in the region of its second leg 30. It is readily possible to compute, from a wall thickness 34 and the angle α, the length of a leg 28, 30, 32 or the point of transition from one leg 28, 30, 32 to the next. Once it is known which leg 28, 30, 32 has hit the flaw 36, the approximate distance between the flaw 36 and the angle beam probe 10 can be inferred; it is at least obvious that the flaw is located on the path portion of the corresponding leg 28, 30, 32.

If the sound hits a flaw 36 such as an air bubble, it is reflected as an echo signal back to the receiver depending on the orientation of the flaw 36.

In accordance with the invention, the measurement data obtained is represented in a cross-sectional image 38 on the display 14 (FIG. 2). The front surface 22 and the rear wall 24 as well as the weld seam 20 are shown by lines in a diagram in which length units are plotted on an x-axis and on a y-axis. Preferably, the sound path 26, which divides into the various legs 28, 30, 32, can still be seen.

For testing the test body 18, the angle beam probe 10 is first placed onto the front surface 22 and ultrasound pulses are insonified into the test body 18 at a certain angle alpha.

If the sound hits a flaw 36, the latter is represented on the display 14, that is, in the cross-sectional image 38, as a first flaw signal 40, preferably according to the comparative method. Accordingly, the inspector has to find the flaw 36 and to grow an optimal first flaw signal 40 from the first position or disposition of the angle beam probe 10. In this context, the term grow means that the inspector tries to find the maximal first flaw signal 40 and to represent it. Using the comparative method, the extension of the flaw 36 with respect to the first disposition of the angle beam probe is determined and the first flaw signal 40 is represented accordingly true to scale on the display 14. A first measurement image is obtained which the inspector stores in the ultrasonic inspection apparatus or in a computer connected thereto.

Then, the same flaw 36 is found and grown from a second position or disposition of the probe so that the extension of the flaw 36 with respect to the second disposition of the angle beam probe is also represented true to scale on the display in a second measurement image as the second flaw signal 42. The inspector stores this measurement image as well.

Finally, the first and the second measurement images are represented concurrently in an evaluation image 44 in such a manner that the first flaw signal 40 and the second flaw signal 42 can be recognized as such. Such an evaluation image 44 is shown in FIG. 2.

In the evaluation image 44 shown in FIG. 2, two measurement images are shown superimposed. This can be seen from the fact that two sound paths 26a, 26b are shown which are reflected from the rear wall 24 at various places and accordingly from the front surface 22 at various places. Advantageously, the two sound paths 26 are shown by different kinds of lines so that they can more readily be distinguished. It can also be seen that the two sound paths 26 have generated one flaw signal 40, 42 each. The flaw signals 40, 42 are also advantageously shown in different representations that may be adapted to the representation of the respective one of the associated leg 28, 30, 32 or of the associated sound path 26. Accordingly, it can readily be seen from which disposition of the angle beam probe 10 the respective signal 40, 42 originates. Also, it may be sensible to show the flaw signals 40, 42 in an encoded, more specifically in a colour-encoded representation, depending on the amplitude determined. Flaws 36 in excess of a certain size may be represented in a signal colour such as red for example.

The flaw signals 40, 42 represented are estimated and displayed true to scale on the display 14 according to a comparative method, that is to say, on the basis of an equivalent reflector size for example. The exemplary representation accordingly shows that the flaw 36 extends more across sound path 26a than across sound path 26b. If further images are superimposed, the image obtained of the flaw 36 is even more accurate.

Accordingly, using the representation of the invention, the user of the ultrasonic inspection apparatus or the inspector gets a very precise idea of the orientation, the size and the volume of the flaw 36.

In a particularly advantageous implementation variant, the data on which the measurement images or the evaluation image 44 are based are further shown in a top view image 46. This signifies that the test body 18 and the weld seam 20 are also shown by lines on the monitor 12 or on the display 14 for example. The data obtained on which the flaw signals 40, 42 are based are converted in such a manner that the extension of the flaw 36 is displayed on the display 14 in the longitudinal plane of the test body 18, meaning in the plane that extends across the cross-sectional image 38. This is also represented in a diagram that comprises length units both on the x- and on the y-axis so that the length and the width of the flaw 36 can readily be seen in the longitudinal plane of the test body 18.

Concurrently to representing the measurement data in accordance with the invention, an A-scan can also be produced. It can be either stored in the background or concurrently displayed on the display 14.

Although various representations, meaning the cross-sectional images 38, the evaluation images 44 and the top view images 46, can be represented concurrently on the display 14, it may be sensible for the inspector to be capable of switching between these representations.

In another advantageous implementation variant, the angle beam probe 10 comprises a calliper for recording the zero point position at the beginning of the inspection procedure. This means that inspection starts at a defined place on the test body, this place being stored in the system. For this purpose, the angle beam probe 10 comprises a means 38 (see FIG. 1) that is solidly connected to the angle beam probe 10 and serves to indicate the respective position on the surface of the body to be tested with respect to the position at the beginning of measurement. This may be achieved using a digital camera that is solidly connected to the housing of the angle beam probe. It is oriented so as to capture the surface of the test body.

The use of a colour display has proved very advantageous because it allows both to simplify and to make more visible the marking of the discrete legs 28, 30, 32 and of the flaw signals 40, 42.

Another advantage of the representation of the invention is that only that region of the test body 18 to be inspected is represented on the monitor 12 or on the display 14 that is of interest for testing. This may for example be the weld seam 20 to be tested. For this purpose, both spatial limits and limits relative to the amplitudes to be taken into consideration are entered into the ultrasonic inspection apparatus and regarded prior to performing the measurement. This means that only those signals are displayed that originate from either the region and/or the environment of the to-be-tested weld seam 20 and/or the intensity of which exceeds the minimal limit and/or remains below the maximal limit.

From what has been said herein above it is obvious that the apparatus of the invention, and in particular the method of inspecting workpieces performed therewith, are suited for serial measurement. An example of a serial measurement is the inspection of weld connections of automobile bodyworks. The inspection apparatus is first adjusted on a workpiece or on a few workpieces prior to performing serial testing.

The invention claimed is:

1. A method of displaying echo signals obtained with the help of an ultrasonic test apparatus for non-destructive testing of a test body, the ultrasonic test apparatus having an angle beam probe, an emitter, which is connected to the angle beam probe and which generates initial pulses which it delivers to the angle beam probe, a receiver, which is connected to the angle beam probe and which receives echo signals, and a monitor with a display, which is connected to the receiver to display the echo signals received in a cross-sectional image in such a manner that at least one front face and one back wall of the test body can be seen, the method comprising:

placing the angle beam probe onto a front face of the test body;

isonifying ultrasonic pulses into the test body at a certain angle;

finding and growing a flaw from a first location of the angle beam probe, the extension of the flaw with respect to the first location of the angle beam probe being obtained with the help of a reference block process and being displayed true-to-scale on the display of the ultrasonic test apparatus as a first flaw signal in a first measurement image;

storing the first measurement image generated and an associated A-scan;

finding and growing the same flaw from a second location of the angle beam probe, the extension of the flaw with respect to the second location of the angle beam probe being obtained with the help of a reference block process and being displayed true-to-scale on the display as a second flaw signal in a second measurement image;

storing the second measurement image generated and an associated A-scan;

displaying the first and the second measurement images in one single evaluation image in such a manner that the first and the second flaw signals can be seen, superposed; and showing in the first and the second measurement images and the evaluation image a sound path that is divided into legs, the different legs being shown differently each and the first and second flaw signals being respectively shown according to the sound path or the leg or both from which they originate.

2. The method as set forth in claim 1, wherein said test body comprises a weld seam, said method further comprising: inspecting the weld seam, and representing said weld seam in the cross-sectional image, the first and second measurement images and the evaluation image.

3. The method as set forth in claim 1, further comprising: representing the received echo signals in a top view image in such a manner that the extension of the flaw extends in the longitudinal plane of the test body, meaning in the plane that extends substantially transverse to the cross-sectional image, is displayed on the display.

4. The method as set forth in claim 1, further comprising: fixedly connecting the angle beam probe to a means that serves to detect the respective position of the angle beam probe on the surface of the test body.

5. The method as set forth in claim 1, further comprising: representing only that region of the test body to be tested and/or such flaw signals is/are represented on the display that is/are of interest for testing, wherein said region of the test body and/or flaw signals is/are determined taking into consideration limit values in terms of amplitude and/or spatial limits.

6. The method as set forth in claim 5, further comprising: encoding the representation of the flaw signals depending on the amplitude determined.

7. The method as set forth in claim 6, wherein said encoding step comprises colour encoding as a function of the amplitude obtained.

8. The method as set forth in claim 1, wherein the flaw is located between the first location and the second location of the angle beam probe.

9. The method as set forth in claim 1, wherein the first location and the second location of the angle beam probe are located on the same side of the flaw but are spaced a different distance from said flaw.

* * * * *